United States Patent
Tanimori et al.

(10) Patent No.: US 11,884,184 B2
(45) Date of Patent: Jan. 30, 2024

(54) INFORMATION PROCESSING DEVICE, INFORMATION PROCESSING METHOD, AND INFORMATION PROCESSING PROGRAM

(71) Applicant: Toyota Jidosha Kabushiki Kaisha, Toyota (JP)

(72) Inventors: Shunsuke Tanimori, Nagoya (JP); Ryota Nakabayashi, Toyota (JP); Osamu Izumida, Nagoya (JP); Takeshi Kanou, Seto (JP); Naoki Yamada, Toyota (JP); Kazuyuki Inoue, Nagoya (JP); Shin Sakurada, Toyota (JP); Hiromitsu Fujii, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 632 days.

(21) Appl. No.: 17/073,704

(22) Filed: Oct. 19, 2020

(65) Prior Publication Data
US 2021/0122246 A1  Apr. 29, 2021

(30) Foreign Application Priority Data
Oct. 29, 2019 (JP) ................... 2019-196718

(51) Int. Cl.
*B60L 7/18* (2006.01)
*G01C 21/34* (2006.01)

(52) U.S. Cl.
CPC ............ *B60L 7/18* (2013.01); *G01C 21/3469* (2013.01); *B60L 2240/60* (2013.01); *B60L 2250/26* (2013.01)

(58) Field of Classification Search
None
See application file for complete search history.

(56) References Cited

U.S. PATENT DOCUMENTS

| | | | |
|---|---|---|---|
| 11,367,121 B2* | 6/2022 | Chow | G06F 16/906 |
| 2013/0046526 A1* | 2/2013 | Yucel | G01C 21/3469 703/8 |
| 2014/0129080 A1* | 5/2014 | Leibowitz | B60R 16/0231 705/26.7 |
| 2015/0073933 A1* | 3/2015 | Stieg | G06Q 30/0631 705/26.7 |
| 2015/0093722 A1* | 4/2015 | Fitzgerald | G09B 9/04 434/62 |
| 2018/0211451 A1* | 7/2018 | Ashton | G07C 5/008 |
| 2018/0225893 A1* | 8/2018 | Brenner | G07C 5/08 |
| 2019/0176656 A1* | 6/2019 | Osgood | G07C 5/008 |
| 2020/0202410 A1* | 6/2020 | Edwards | G06Q 30/0641 |
| 2020/0311796 A1* | 10/2020 | Tang | G06Q 30/0631 |
| 2021/0082073 A1* | 3/2021 | Crespo | G06Q 50/30 |
| 2021/0166103 A1* | 6/2021 | Jackson | G06N 3/088 |

FOREIGN PATENT DOCUMENTS

JP  2002-269401 A  9/2002

\* cited by examiner

*Primary Examiner* — Adam D Tissot
*Assistant Examiner* — Garrett F Evans
(74) *Attorney, Agent, or Firm* — Dinsmore & Shohl LLP

(57) ABSTRACT

An information processing device includes a control unit configured to determine whether to include a regenerative brake in specifications of a proposed vehicle based on regenerative brake operation data acquired while a first vehicle including the regenerative brake is traveling in a predetermined area. The proposed vehicle is a vehicle proposed as a vehicle for a customer to drive in the predetermined area.

19 Claims, 3 Drawing Sheets

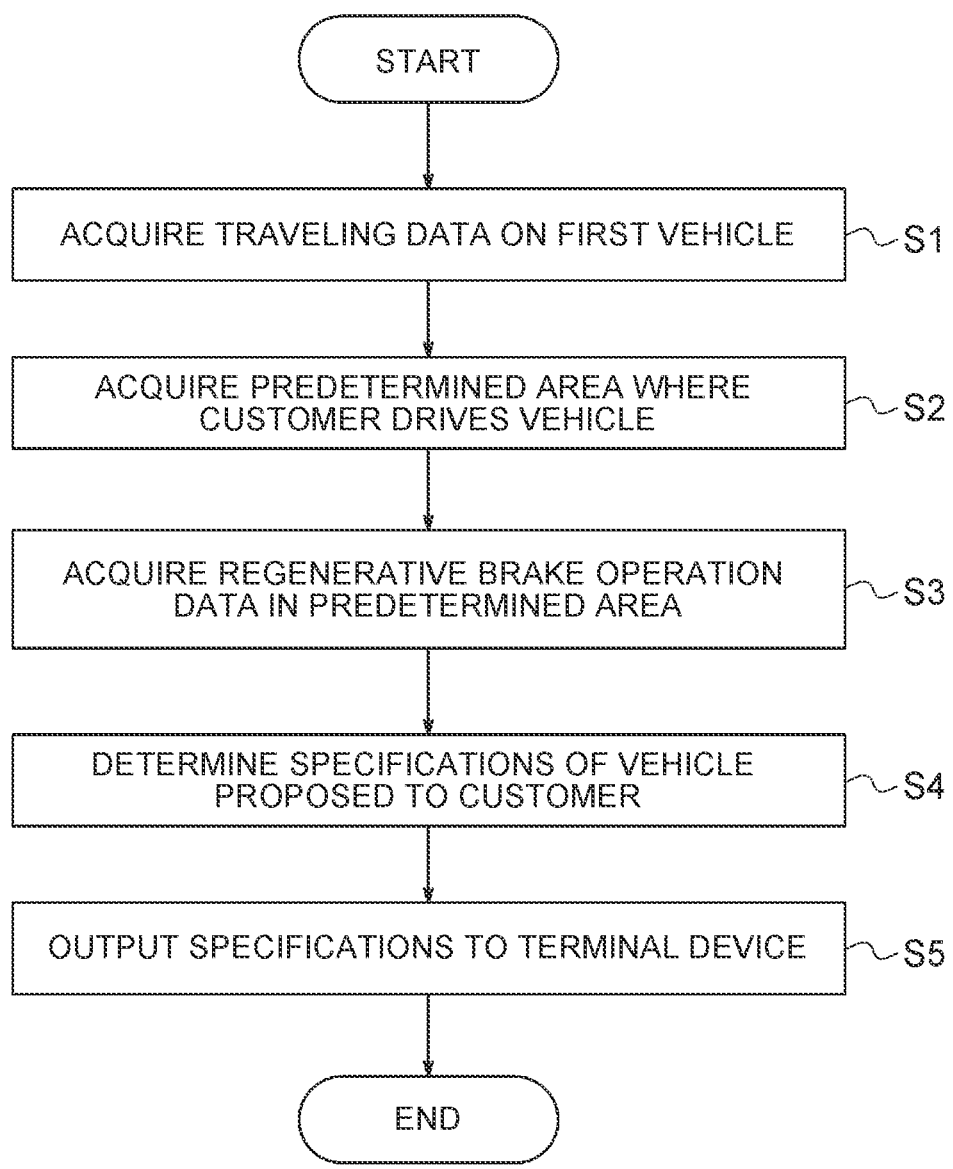

INFORMATION PROCESSING DEVICE, INFORMATION PROCESSING METHOD, AND INFORMATION PROCESSING PROGRAM

CROSS-REFERENCE TO RELATED APPLICATIONS

This application claims priority to Japanese Patent Application No. 2019-196718 filed on Oct. 29, 2019, which is incorporated herein by reference in its entirety including the specification, drawings and abstract.

BACKGROUND

1. Technical Field

The present disclosure relates to an information processing device, an information processing method, and an information processing program.

2. Description of Related Art

Conventionally, a device for ordering a car is known. For example, Japanese Unexamined Patent Application Publication No. 2002-269401 (JP 2002-269401 A) discloses a car sales order device that allows a customer to set the specifications of each of the parts of a car.

SUMMARY

The specifications that are set based on the preferences of a customer may not be suitable for the environment in which the customer uses a vehicle.

The present disclosure provides an information processing device, an information processing method, and an information processing program that make the vehicle specifications, which are proposed to a customer, more suitable for the environment in which the vehicle is used.

A first aspect of the present disclosure relates to an information processing device including a control unit. The control unit is configured to determine whether to include a regenerative brake in specifications of a proposed vehicle based on regenerative brake operation data acquired while a first vehicle including the regenerative brake is traveling in a predetermined area. The proposed vehicle is a vehicle proposed as a vehicle for a customer to drive in the predetermined area.

A second aspect of the present disclosure relates to an information processing method. The information processing method includes determining whether to include a regenerative brake in specifications of a proposed vehicle based on regenerative brake operation data acquired while a first vehicle including the regenerative brake is traveling in a predetermined area. The proposed vehicle is a vehicle proposed as a vehicle for a customer to drive in the predetermined area.

A third aspect of the present disclosure relates to an information processing program. The information processing program causes a processor to determine whether to include a regenerative brake in specifications of a proposed vehicle based on regenerative brake operation data acquired while a first vehicle including the regenerative brake is traveling in a predetermined area. The proposed vehicle is a vehicle proposed as a vehicle for a customer to drive in the predetermined area.

According to the information processing device, information processing method, and information processing program according to one embodiment of the present disclosure, it is possible to make the specifications of a vehicle, which are proposed to a customer, more suitable for the usage environment of the customer.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 3 is a flowchart showing an example of a procedure of an information processing method according to one embodiment.

DETAILED DESCRIPTION OF EMBODIMENTS

A vehicle dealer is sometimes required to propose to a customer a vehicle that has specifications suitable for the manner in which the vehicle is driven by the customer. As one of the specifications of a vehicle proposed to the customer, the dealer can select the type of the prime mover mounted on the vehicle. For example, the dealer can propose to the customer, at least one of a vehicle equipped with only an engine as the prime mover, a vehicle equipped with only a motor as the prime mover, and a vehicle equipped with an engine and a motor as the prime mover.

Configuration Example of Information Processing System 1

Figure 1:
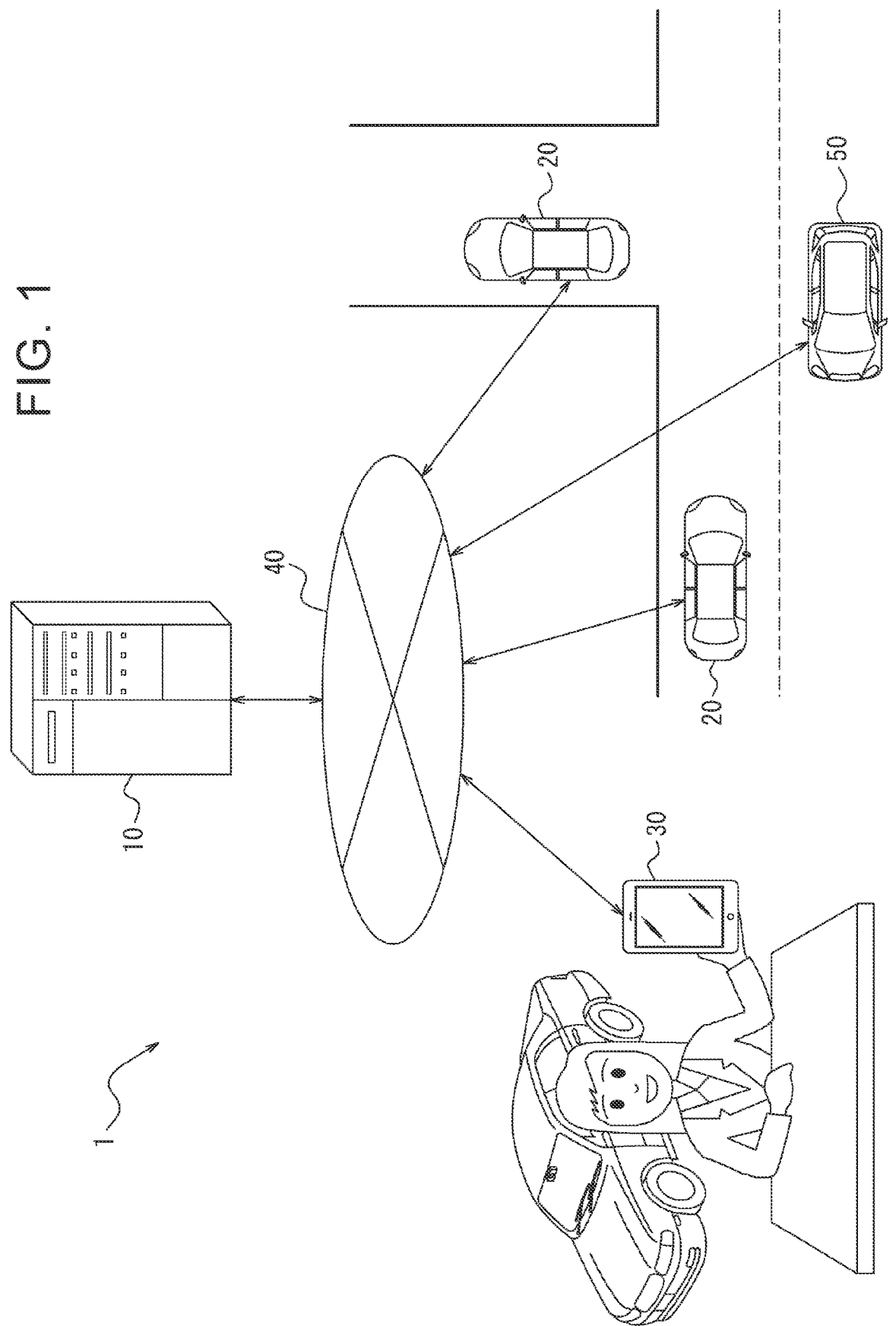
FIG. 1 is a schematic diagram showing a configuration example of an information processing system according to one embodiment.
Figure 2:
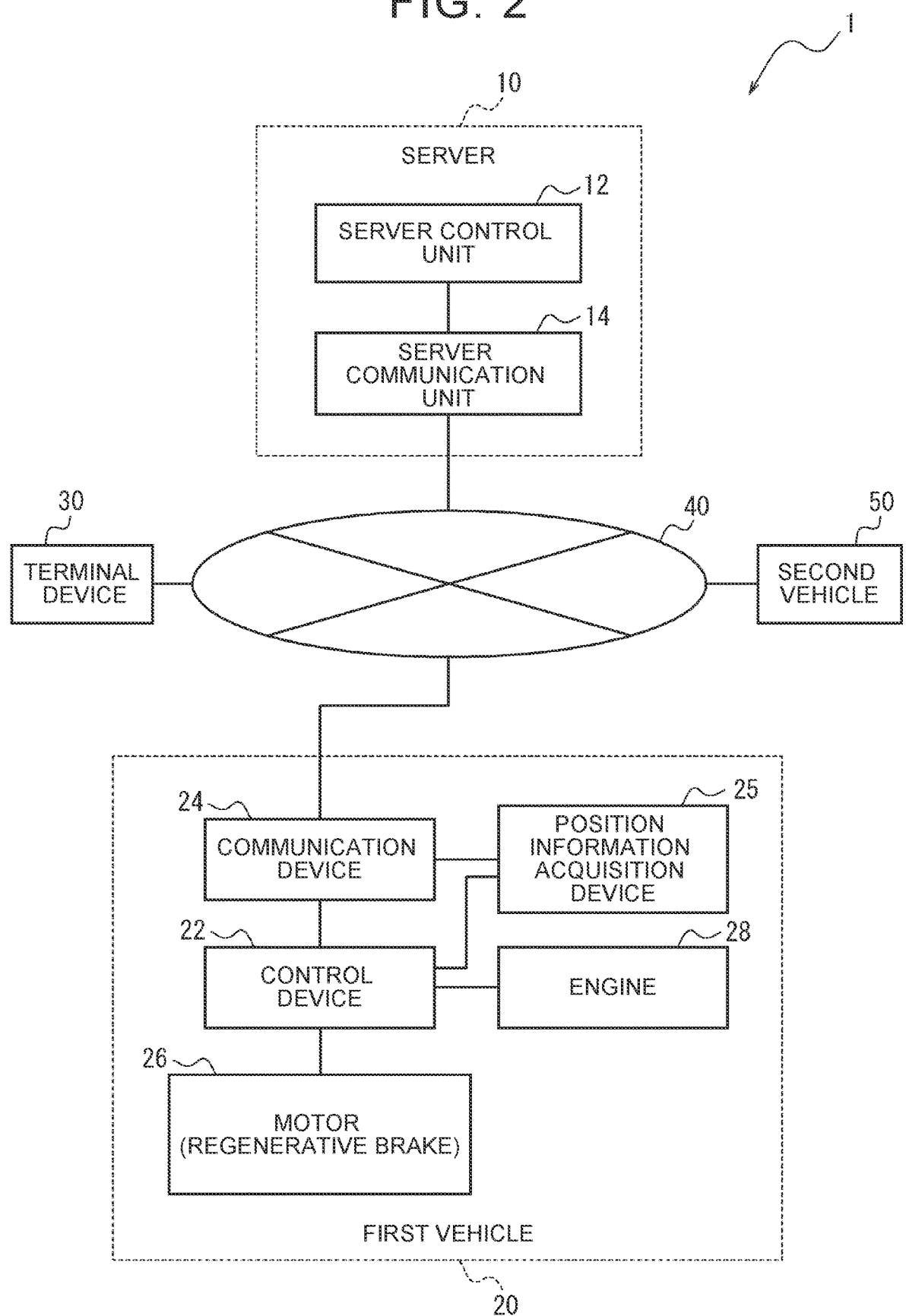
FIG. 2 is a block diagram showing a configuration example of the information processing system according to one embodiment.

As shown in FIG. 1 and FIG. 2, an information processing system 1 according to one embodiment includes a server 10, a first vehicle 20, and a terminal device 30. The server 10, first vehicle 20, and terminal device 30 are connected to a network 40. The information processing system 1 includes a second vehicle 50 though it is not always required. The second vehicle 50 is connected to the server 10 via the network 40.

Configuration Example of Server 10

The server 10 is configured to be able to communicate with the first vehicle 20, second vehicle 50, and terminal device 30, respectively. The number of each of servers 10, first vehicles 20, second vehicles 50, and terminal devices 30 is not limited to one but may be two or more. The server 10 is also called an information processing device. The server 10 may include one server device or a plurality of server devices that can communicate with each other.

The server 10 includes a server control unit 12 and a server communication unit 14. The server control unit 12 is also simply referred to as a control unit. The server control unit 12 may include one or more processors. In this embodiment, a "processor" is a general-purpose processor or a dedicated processor specialized for specific processing but is not limited thereto. The server control unit 12 may include one or more dedicated circuits. The dedicated circuit may include, for example, a field-programmable gate array (FPGA) or an application specific integrated circuit (ASIC). The server control unit 12 may include a dedicated circuit instead of a processor or may include a dedicated circuit together with a processor. The server communication unit 14 may include a communication module for communication with the first vehicle 20 or the second vehicle 50 via the network 40. The server 10 may further include a storage unit. The storage unit is, for example, a semiconductor memory, a magnetic memory, or an optical memory but is not limited thereto. The storage unit may function, for example, as a main storage device, an auxiliary storage device, or a cache memory. The storage unit may include an electromagnetic storage medium such as a magnetic disk. The storage unit stores any information used for the operation of the server 10. For example, the storage unit may store the system program and application programs.

Configuration Example of First Vehicle 20

The first vehicle 20 includes a control device 22 and a communication device 24. The control device 22 and the communication device 24 are communicably connected to each other via an in-vehicle network such as a controller area network (CAN) or via a dedicated line.

The control device 22 controls the components included in the first vehicle 20. The control device 22 may include one or more processors. The control device 22 may include one or more dedicated circuits instead of processors or may include processors and one or more dedicated circuits. The control device 22 may further include a storage unit.

The communication device 24 is communicatively connected to the server 10 via the network 40. The communication device 24 may be, for example, an in-vehicle communication device. The communication device 24 may include a communication module that connects to the network 40. The communication module may include a communication module compatible not only with a mobile communication standard such as the fourth generation (4G) standard and the fifth generation (5G) standard but also with other communication modules.

The first vehicle 20 further includes a motor 26. The motor 26 functions not only as a prime mover for driving the first vehicle 20 but also as a regenerative brake. That is, the first vehicle 20 includes a regenerative brake. The first vehicle 20 may include a regenerative brake as a component different from the motor 26.

The first vehicle 20 further includes an engine 28 though it is not always required. The first vehicle 20 that includes both the motor 26 and the engine 28 is also referred to as a hybrid electric vehicle. The first vehicle 20 that includes the motor 26 but does not include the engine 28 is also referred to as an electric vehicle. The first vehicle 20 that includes the motor 26 is also referred to as an electrically powered vehicle regardless of whether or not the first vehicle 20 includes the engine 28.

The control device 22 controls the motor 26 and the engine 28 to control the traveling and braking of the first vehicle 20.

The first vehicle 20 further includes a position information acquisition device 25 though it is not always required. The position information acquisition device 25 is communicably connected to the control device 22 or the communication device 24 via an in-vehicle network such as CAN or via a dedicated line. The position information acquisition device 25 acquires the position information on the first vehicle 20. The position information acquisition device 25 may include a receiver corresponding to the satellite positioning system. The receiver corresponding to the satellite positioning system may include, for example, a global positioning system (GPS) receiver. The first vehicle 20 can acquire the position information on the first vehicle 20 itself using the position information acquisition device 25. The first vehicle 20 may output the position information on the first vehicle 20 itself to the server 10.

The second vehicle 50 may have a configuration the same as, or similar to, the configuration of the first vehicle 20. The second vehicle 50 may include only the engine 28 without including the motor 26.

Configuration Example of Terminal Device 30

The terminal device 30 may include a personal computer (PC) such as a desktop PC, a notebook PC, or a tablet PC or may include a mobile terminal such as a smartphone. The terminal device 30 is communicably connected by a cable or wirelessly to the server 10 via the network 40.

The terminal device 30 may be operated by a clerk of a vehicle dealer as shown in FIG. 1. The terminal device 30 may also be operated by a customer who is considering to buy a vehicle. The terminal device 30 may run an application that is operated by a clerk or a customer for displaying the specifications of a vehicle suitable for the customer. The terminal device 30 outputs to the server 10 the information that is requested by the server 10 and, at the same time, acquires the information that is output from the server 10.

The terminal device 30 may receive an input of information required by the server 10 to determine the vehicle specifications suitable for a customer. The terminal device 30 may send the received information to the server 10. The application may acquire the information on the specifications of the vehicle, suitable for the customer, from the server 10 and may cause the terminal device 30 to display the acquired information.

The terminal device 30 may include an input device for receiving an operation by a clerk or a customer. The input device may include, for example, a keyboard or physical keys or may include a pointing device such as a touch panel or a touch sensor, or a mouse.

When the specifications of the vehicle suitable for the customer are acquired from the server 10, the terminal device 30 may display the acquired specifications. The terminal device 30 may include a display device such as a liquid crystal display device, an organic electro-luminescence (EL) display device, or an inorganic EL display device. The terminal device 30 may be connected to an external display device for displaying the vehicle specifications on it. A clerk may propose a vehicle to the customer based on the specifications displayed on the terminal device 30. A customer may consider whether to buy a vehicle based on the specifications displayed on the terminal device 30.

Operation Example of Information Processing Device

The server control unit 12 of the server 10 (information processing device) may execute an information processing method including, for example, the procedure of the flowchart shown in FIG. 3. The information processing method may be implemented as an information processing program that is executed by a processor such as the server control unit 12.

The server control unit 12 acquires the traveling data on the first vehicle 20 (step S1). The first vehicle 20 may include a vehicle driven by a customer or may include a vehicle driven by a person other than the customer. The first vehicle 20 may also include a vehicle traveling autonomously. Autonomous driving may be performed at any one of levels 1 to 5 defined, for example, by the Society of Automotive Engineers (SAE). The levels of autonomous driving are not limited to the definition described above but any other definition may also be used. The first vehicle 20 may include at least one of an electric vehicle and a hybrid electric vehicle. That is, the server control unit 12 may acquire the traveling data on at least one of an electric vehicle and a hybrid electric vehicle.

The server control unit 12 acquires a predetermined area where the customer drives the vehicle (step S2). The predetermined area corresponds to an area where the customer travels by driving the vehicle.

The predetermined area may include an area where the customer drives the vehicle on a daily basis. The predetermined area may include an area where the customer travels the vehicle for a length of time with a ratio equal to or higher than a predetermined ratio with respect to the total time during which the customer drives the vehicle. The predetermined ratio may be, for example, 50% or 80%. The predetermined ratio is not limited to these ratios but various ratios may be used.

The server control unit 12 may acquire the information specifying the predetermined area from the terminal device 30. The terminal device 30 may allow a clerk or a customer to enter the information specifying the predetermined area. The server control unit 12 may determine the predetermined area based on the information specifying the predetermined area.

The server control unit 12 may acquire, from the terminal device 30, the information that identifies the second vehicle 50 that has been driven by the customer. The server control unit 12 may acquire the traveling data from the second vehicle 50 and, based on the acquired traveling data, determine the predetermined area. The second vehicle 50 may include a vehicle owned by the customer. The second vehicle 50 may include a vehicle used by the customer in business. The second vehicle 50 may include a rental car rented by the customer.

The server control unit 12 acquires the regenerative brake operation data in the predetermined area (Step S3). The server control unit 12 may acquire the regenerative brake operation data in the predetermined area based on the traveling data acquired while the first vehicle 20 was traveling in the predetermined area. The regenerative brake operation data may be included in the traveling data. The server control unit 12 may acquire the position information on the first vehicle 20 from the position information acquisition device 25 of the first vehicle 20. Based on the position information on the first vehicle 20 acquired in this way, the server control unit 12 may determine whether the first vehicle 20 is traveling in the predetermined area.

The regenerative brake operation data may include the number of times the regenerative brake was operated per unit distance or per unit time. The regenerative brake operation data may include the amount of power recovered by the operation of the regenerative brake. The regenerative brake operation data may include the average value of the power recovered by the operation of the regenerative brake over the traveling time of the first vehicle 20.

The server control unit 12 determines the specifications of the vehicle proposed to the customer based on the regenerative brake operation data in the predetermined area (step S4). The vehicle proposed to the customer is also referred to as a proposed vehicle. The server control unit 12 may determine whether the specifications including the regenerative brake are appropriate as the specifications of a vehicle traveling in the predetermined area, based on the regenerative brake operation data acquired in the predetermined area.

The server control unit 12 outputs the determined specifications to the terminal device 30 (step S5). After performing the procedure in step S5, the server control unit 12 terminates the execution of the flowchart in FIG. 3. The terminal device 30 displays the specifications acquired from the server control unit 12. Based on the specifications displayed on the terminal device 30, the clerk of the vehicle dealer may propose a vehicle suitable for the manner in which the vehicle is driven by the customer. The customer may consider what vehicle to buy based on the specifications displayed on the terminal device 30.

According to the information processing system 1 and the server 10 (information processing device), the information processing method, and the information processing program in this embodiment, it is possible to make the specifications of a proposed vehicle more suitable for the usage environment of the customer.

Example of Method for Acquiring Regenerative Brake Operation Data

The traveling data may include the information on the times at which the regenerative brake was operated. In the procedure of step S3, this information allows the server control unit 12 to acquire, as the regenerative brake operation data, the number of times the regenerative brake was used.

The traveling data may include the information on a temporal change in the regenerative energy generated by the operation of the regenerative brake. In the procedure of step S3, this information allows the server control unit 12 to acquire the regenerative energy as the regenerative brake operation data.

The traveling data may further include the information on a temporal change in the speed of the first vehicle 20. The server control unit 12 may calculate energy lost due to friction braking based on the relationship between the speed of the first vehicle 20 and the regenerative energy. The energy lost by friction braking is also called loss energy. In the procedure of step S3, this information allows the server control unit 12 to acquire the relationship between the loss energy and the regenerative energy as the regenerative brake operation data.

In the procedure of step S3, the server control unit 12 may acquire the regenerative brake operation data in the predetermined area based on the traveling data on a plurality of the first vehicles 20. The server control unit 12 may calculate the average or the variance of the regenerative brake operation data on the plurality of the first vehicles 20. The server control unit 12 may perform various types of statistical processing for the regenerative brake operation data. Using the result of the statistical processing (such as the calculation of the average or the variance) as the regenerative brake operation data, the server control unit 12 may determine the specifications of the proposed vehicle in the procedure of step S4.

The regenerative brake operation data is acquired using various methods as described above. This makes it easy to recognize the effectiveness of the regenerative brake in the area where the customer drives the vehicle. As a result, it is possible to make the specifications of the proposed vehicle more suitable for the vehicle usage environment of the customer.

Example of Conditions for Determining Specifications

The server control unit 12 may calculate the use rate of the regenerative brake in the procedure of step S4. The use rate of the regenerative brake may be calculated as a value obtained by dividing the number of times the regenerative brake was used by the total number of times the friction brake and the regenerative brake were used. The use rate of the regenerative brake may also be calculated as a value obtained by dividing the regenerative energy by the sum of the loss energy and the regenerative energy. When the use rate of the regenerative brake is equal to or higher than a predetermined value, the server control unit 12 may determine that the specifications including the regenerative brake are suitable as the specifications of a vehicle traveling in the predetermined area. When the use rate of the regenerative brake is lower than the predetermined value, the server control unit 12 may determine that the specifications not including the regenerative brake are suitable as the specifications of a vehicle traveling in the predetermined area. The predetermined value may be set, for example, to 50% but is not limited thereto, and may be set to another value.

The server control unit 12 may determine the frequency-of-use level of the regenerative brake in the procedure of step S4. The frequency-of-use level may be classified, for example, into high, medium, and low. When the use rate of the regenerative brake is equal to or higher than a first predetermined value, the server control unit 12 may determine the frequency-of-use level to be high. When the use rate of the regenerative brake is lower than a second predetermined value, the server control unit 12 may determine the frequency-of-use level to be low. When the use rate of the regenerative brake is equal to or higher than the second predetermined value and is lower than the first predetermined value, the server control unit 12 may determine the frequency-of-use level to be medium. The first predetermined value is larger than the second predetermined value. The first predetermined value and the second predetermined value may be set, for example, to 70% and 30%, respectively, but are not limited thereto and may be set to other values. When the frequency-of-use level of the regenerative brake is high, the server control unit 12 may determine that the specifications including the regenerative brake are suitable as the specifications of a vehicle traveling in the predetermined area. When the frequency-of-use level of the regenerative brake is high or medium, the server control unit 12 may determine that the specifications including the regenerative brake are suitable as the specifications of a vehicle traveling in the predetermined area. When the frequency-of-use level of the regenerative brake is medium or low, the server control unit 12 may determine that the specifications not including the regenerative brake are suitable as the specifications of a vehicle traveling in the predetermined area. When the frequency-of-use level of the regenerative brake is low, the server control unit 12 may determine that the specifications not including the regenerative brake are suitable as the specifications of a vehicle traveling in the predetermined area.

In the procedure of step S4, the server control unit 12 may calculate the ratio between the motion energy lost during the braking of the vehicle and the regenerative energy recovered by the operation of the regenerative brake. When the ratio of the regenerative energy is equal to or higher than a predetermined value, the server control unit 12 may determine that the specifications including the regenerative brake are suitable as the specifications of a vehicle traveling in the predetermined area. When the ratio of the regenerative energy is lower than the predetermined value, the server control unit 12 may determine that the specifications not including the regenerative brake are suitable as the specifications of a vehicle traveling in the predetermined area. The predetermined value may be set, for example, to 50%, but is not limited to this and may be set to another value.

As described above, the specifications of a proposed vehicle are determined based on various conditions related to the regenerative brake operation data. Determining the specifications in this way makes it possible to appropriately select the criteria for recognizing the effectiveness of the regenerative brake in the area where the customer drives the vehicle. As a result, it is possible to make the specifications of the proposed vehicle more suitable for the vehicle usage environment of the customer.

Example of Procedure for Determining Predetermined Area

The terminal device 30 may request a clerk or a customer to specify specific roads on the map for generating the information specifying the predetermined area. The information generated in this way allows the server control unit 12 to determine the specified roads as the predetermined area.

The terminal device 30 may request a clerk or a customer to specify an area on the map for generating the information specifying the predetermined area. The information generated in this way allows the server control unit 12 to determine, as the predetermined area, the roads included the specified area.

When determining the predetermined area based on the traveling data on the second vehicle 50, the server control unit 12 may determine, as the predetermined area, the routes on which the second vehicle 50 has traveled at least once. A route on which the second vehicle 50 has traveled at least once is also referred to as a traveled route. The server control unit 12 may determine, as the predetermined area, the routes that are included in the traveled routes of the second vehicle 50 and on which the second vehicle 50 has traveled a predetermined number of times or more. The predetermined number of times may be, for example, two, but is not limited to this and may be set as appropriate.

The server control unit 12 may determine, as the predetermined area, not only the traveled routes of the second vehicle 50 but also branch roads each of which is a road leading to one of the traveled routes and is within a predetermined distance from the traveled route.

The information specifying the predetermined area may include the information on a day of the week or a time zone when the customer uses the vehicle. For example, the information specifying the predetermined area may be distinguished into two types of areas: the areas where the customer uses the vehicle on weekdays and the areas where the customer uses the vehicle on a holiday such as Saturday, Sunday, or a holiday. For example, the information specifying the predetermined area may be distinguished into two types of area: the areas where the customer uses the vehicle in a commuting time zone from 7:00 to 10:00 or from 17:00 to 19:00 and the areas where the customer uses the vehicle during a non-commuting time zone. When the information relating to the date and time is associated with the information specifying the predetermined area in this way, the server control unit 12 may acquire the regenerative brake operation data based on the traveling data on the first vehicle 20 on a predetermined day of the week or in a predetermined time zone.

The predetermined area in which the customer uses the vehicle is specified by various methods as described above. This makes it easy to recognize the effectiveness of the regenerative brake in various environments in which the customer actually drives the vehicle. As a result, it is possible to make the specifications of the proposed vehicle more suitable for the vehicle usage environment of the customer.

Although the embodiment according to the present disclosure has been described based on the drawings and the embodiment, it should be noted that those skilled in the art can easily make various changes and modifications based on the present disclosure. Therefore, it should be noted that these variations and modifications are included in the scope of the present disclosure. For example, the functions included in each step can be rearranged so as not to be logically inconsistent, and a plurality of steps can be combined into one or can be divided.

What is claimed is:

1. An information processing system device comprising:
   a terminal device; and
   a control unit configured to:
      determine whether to include a proposed regenerative brake in specifications of a proposed vehicle based on regenerative brake operation data acquired while a first vehicle including the regenerative brake is traveling in a predetermined area, the proposed vehicle includes the determined specifications for a customer to drive in the predetermined area; and
      wirelessly output the information on the determined specifications of the proposed vehicle suitable for the customer,
   wherein the terminal device is configured to wirelessly receive the information on the determined specifications of the proposed vehicle suitable for the customer and display the information on the determined specifications of the vehicle suitable for the customer.

2. The information processing system according to claim 1, wherein the control unit is configured to acquire traveling data on at least one of an electric vehicle and a hybrid electric vehicle as traveling data on the first vehicle and to acquire the regenerative brake operation data based on the traveling data on the first vehicle.

3. The information processing system according to claim 1, wherein the control unit is configured to acquire, as the regenerative brake operation data, a number of times the regenerative brake was operated.

4. The information processing system according to claim 1, wherein the control unit is configured to acquire, as the regenerative brake operation data, regenerative energy generated by an operation of the regenerative brake.

5. The information processing system according to claim 1, wherein the control unit is configured to acquire a use rate of the regenerative brake as the regenerative brake operation data.

6. The information processing system according to claim 1, wherein the control unit is configured to receive an input specifying the predetermined area from the customer.

7. The information processing system according to claim 1, wherein the control unit is configured to determine the predetermined area based on traveling data on a second vehicle owned by the customer.

8. The information processing system according to claim 7, wherein the control unit is configured to determine, as the predetermined area, an area including routes on which the second vehicle has traveled and on which the second vehicle has traveled a predetermined number of times or more.

9. The information processing system according to claim 7, wherein the control unit is configured to determine, as the predetermined area, an area including routes on which the second vehicle has traveled and branch roads each of which is within a predetermined distance from one of the routes on which the second vehicle has traveled.

10. An information processing method comprising:
    determining whether to include a proposed regenerative brake in specifications of a proposed vehicle based on regenerative brake operation data acquired while a first vehicle including the regenerative brake is traveling in a predetermined area, the proposed vehicle includes the determined specifications for a customer to drive in the predetermined area;
    wirelessly outputting the information on the determined specifications of the vehicle suitable for the customer; and
    in response to the output, displaying by a terminal device the information wirelessly received on the determined specifications of the vehicle suitable for the customer.

11. The information processing method according to claim 10, the information processing method further comprising acquiring the regenerative brake operation data based on traveling data on the first vehicle that includes at least one of an electric vehicle and a hybrid electric vehicle.

12. The information processing method according to claim 10, the information processing method further comprising acquiring, as the regenerative brake operation data, a number of times the regenerative brake was operated.

13. The information processing method according to claim 10, the information processing method further comprising acquiring, as the regenerative brake operation data, regenerative energy generated by an operation of the regenerative brake.

14. The information processing method according to claim 10, the information processing method further comprising acquiring a use rate of the regenerative brake as the regenerative brake operation data.

15. The information processing method according to claim 10, the information processing method further comprising receiving an input specifying the predetermined area from the customer.

16. The information processing method according to claim 10, the information processing method further comprising determining the predetermined area based on traveling data on a second vehicle owned by the customer.

17. A non-transitory storage medium that stores an information processing program causing a processor to:
    determine whether to include a proposed regenerative brake in specifications of a proposed vehicle based on regenerative brake operation data acquired while a first vehicle including the regenerative brake is traveling in a predetermined area, the proposed vehicle includes the determined specifications for a customer to drive in the predetermined area; and
    wirelessly output the information on the determined specifications of the vehicle suitable for the customer,
    wherein a terminal device is configured to wirelessly receive the information on the specifications of the vehicle suitable for the customer and display the information on the determined specifications of the vehicle suitable for the customer.

18. The information processing system of claim 1, wherein the control unit is further configured to:
- communicate with the first vehicle and the terminal device via wireless communication;
- receive traveling data transmitted by the first vehicle via wireless communication; and
- acquire the regenerative brake operation data based on the received traveling data.

19. The information processing system of claim 1, further comprising:
- an information processing device including the control unit,
- wherein the terminal device includes a display.

* * * * *